(12) United States Patent
Karssemeijer et al.

(10) Patent No.: US 10,242,490 B2
(45) Date of Patent: Mar. 26, 2019

(54) DISPLAYING SYSTEM FOR DISPLAYING DIGITAL BREAST TOMOSYNTHESIS DATA

(71) Applicant: ScreenPoint Medical, Nijmegen (NL)

(72) Inventors: Nico Karssemeijer, Beek (NL); Albert Gubern-Mérida, Den Bosch (NL)

(73) Assignee: ScreenPoint Medical, Nijmegen (NL)

( * ) Notice: Subject to any disclaimer, the term of this patent is extended or adjusted under 35 U.S.C. 154(b) by 35 days.

(21) Appl. No.: 15/821,727

(22) Filed: Nov. 22, 2017

(65) Prior Publication Data

US 2018/0158228 A1 Jun. 7, 2018

(30) Foreign Application Priority Data

Nov. 25, 2016 (EP) .................................... 16200820

(51) Int. Cl.
*A61B 6/02* (2006.01)
*A61B 6/00* (2006.01)
(Continued)

(52) U.S. Cl.
CPC .............. *G06T 15/08* (2013.01); *A61B 6/025* (2013.01); *A61B 6/463* (2013.01); *A61B 6/466* (2013.01);
(Continued)

(58) Field of Classification Search
CPC ......... A61B 6/025; A61B 6/466; A61B 6/502; A61B 10/0041; A61B 90/39;
(Continued)

(56) References Cited

U.S. PATENT DOCUMENTS

2004/0094167 A1 5/2004 Brady et al.
2007/0177780 A1 8/2007 Chui
(Continued)

FOREIGN PATENT DOCUMENTS

JP 2017-042422 3/2017
JP 2017-042423 3/2017

OTHER PUBLICATIONS

European Search Report completed May 12, 2017, in European Patent Application No. 16200820, 5 pages.
(Continued)

*Primary Examiner* — Ke Xiao
*Assistant Examiner* — Andrew Shin
(74) *Attorney, Agent, or Firm* — Ellen M. Bierman; Lowe Graham Jones PLLC

(57) ABSTRACT

The invention relates to a displaying system for displaying digital breast tomosynthesis (DBT) data. First and second DBT volume images of the left breast of a woman and first and second DBT volume images of the right breast of the woman are provided by an image providing unit. Moreover, for each DBT volume image a two-dimensional navigation image is provided by a navigation image providing unit, wherein a user is allowed to indicate a location in the navigation image by using a user interface, whereafter a CAD marker associated with the location is determined in a DBT volume image of a breast and a corresponding CAD marker, if present, is determined in another DBT volume image of the breast. Slices of these DBT volume images, which are associated with the CAD markers, are presented on a display.

20 Claims, 5 Drawing Sheets

(51) Int. Cl.
*G06T 7/00* (2017.01)
*G06T 19/00* (2011.01)
*G06T 15/08* (2011.01)
*G06T 7/73* (2017.01)
*A61B 8/08* (2006.01)
*A61B 8/00* (2006.01)
*G06K 9/62* (2006.01)

(52) U.S. Cl.
CPC ............ *A61B 8/0825* (2013.01); *A61B 8/467* (2013.01); *G06K 9/6201* (2013.01); *G06T 7/0012* (2013.01); *G06T 7/0014* (2013.01); *G06T 7/0016* (2013.01); *G06T 7/73* (2017.01); *G06T 19/003* (2013.01); *G06T 2200/24* (2013.01); *G06T 2207/10112* (2013.01); *G06T 2207/20076* (2013.01); *G06T 2207/30068* (2013.01); *G06T 2207/30096* (2013.01); *G06T 2207/30204* (2013.01); *G06T 2210/41* (2013.01)

(58) Field of Classification Search
CPC ............ A61B 2090/3908; G06K 9/62; G06K 9/6201; G06K 9/6202; G06T 7/0012; G06T 7/0016; G06T 19/003; G06T 15/08; G06T 7/0014; G06T 2207/30068; G06T 2210/41
See application file for complete search history.

(56) References Cited

U.S. PATENT DOCUMENTS

2011/0289441 A1    11/2011  Venon et al.
2012/0014578 A1*    1/2012  Karssemeijer ........ G06T 7/0012
                                              382/131
2016/0220210 A1     8/2016  Ruth et al.
2017/0055929 A1*    3/2017  Machida ............. A61B 6/5235

OTHER PUBLICATIONS

Rafferty, E, Niklason, L, Jameson-Meehan, L, Breast Tomosynthesis: One View or Two?. Radiological Society of North America 2006 Scientific Assembly and Annual Meeting, Nov. 26-Dec. 1, 2006, Chicago IL. http://archive.rsna.org/2006/4430594.html Accessed Jun. 14, 2018.

van Schie et al., "Generating Synthetic Mammograms From Reconstructed Tomosynthesis Volumes," IEEE Transactions on Medical Imaging, vol. 32, No. 12, Dec. 2013, pp. 2322-2331.

van Schie et al., "Mass detection in reconstructed digital breast tomosynthesis volumes with a computer-aided detection system trained on 2D mammograms," Med. Phys. 40(4), Apr. 2013, 11 pages.

* cited by examiner

DISPLAYING SYSTEM FOR DISPLAYING DIGITAL BREAST TOMOSYNTHESIS DATA

FIELD

The invention relates to a displaying system, method and computer program for displaying digital breast tomosynthesis (DBT) data.

BACKGROUND

Two-dimensional x-ray mammography is currently the gold standard for the detection of breast cancer in its early stages. However, a limitation of this modality is that in a two-dimensional projection of the breast superimpositions of normal tissue may look suspicious and lead to false positives while reviewing two-dimensional x-ray mammography images. Moreover, true lesions can be obscured by overlying breast tissue. In order to diminish these problems, usually two views of each breast are acquired for examining the respective breast, i.e. a craniocaudal (CC) view and a mediolateral oblique (MLO) view, wherein the MLO view is acquired at an angle between 30 degrees and 60 degrees from the CC view.

DBT was introduced as a promising modality to overcome these projection problems, wherein DBT includes a reconstruction of a three-dimensional volume of the breast from several low dose, limited angle x-ray projections. With the introduction of DBT it was suggested that by adding the third dimension only one tomosynthesis view per breast would be required. However, recent insights indicate that in DBT also two views may be required, in order to optimally visualize lesions, as disclosed, for instance, in the article "Breast tomosynthesis: one view or two?" by E. A. Rafferty et al., Meeting Radiological Society of North America, page 335 (2006).

If DBT volume images corresponding to different views need to be reviewed for detecting breast cancer, information from both views need to be combined. However, since the DBT volume images comprise many slices, combining information from the different views is very difficult and time consuming for a radiologist.

SUMMARY

A displaying system, a displaying method and a computer readable storage medium containing program code, instructions, or logic which assist a radiologist in combining information from different DBT volume images, for example, of a woman's breast are provided.

DETAILED DESCRIPTION

Figure 1:
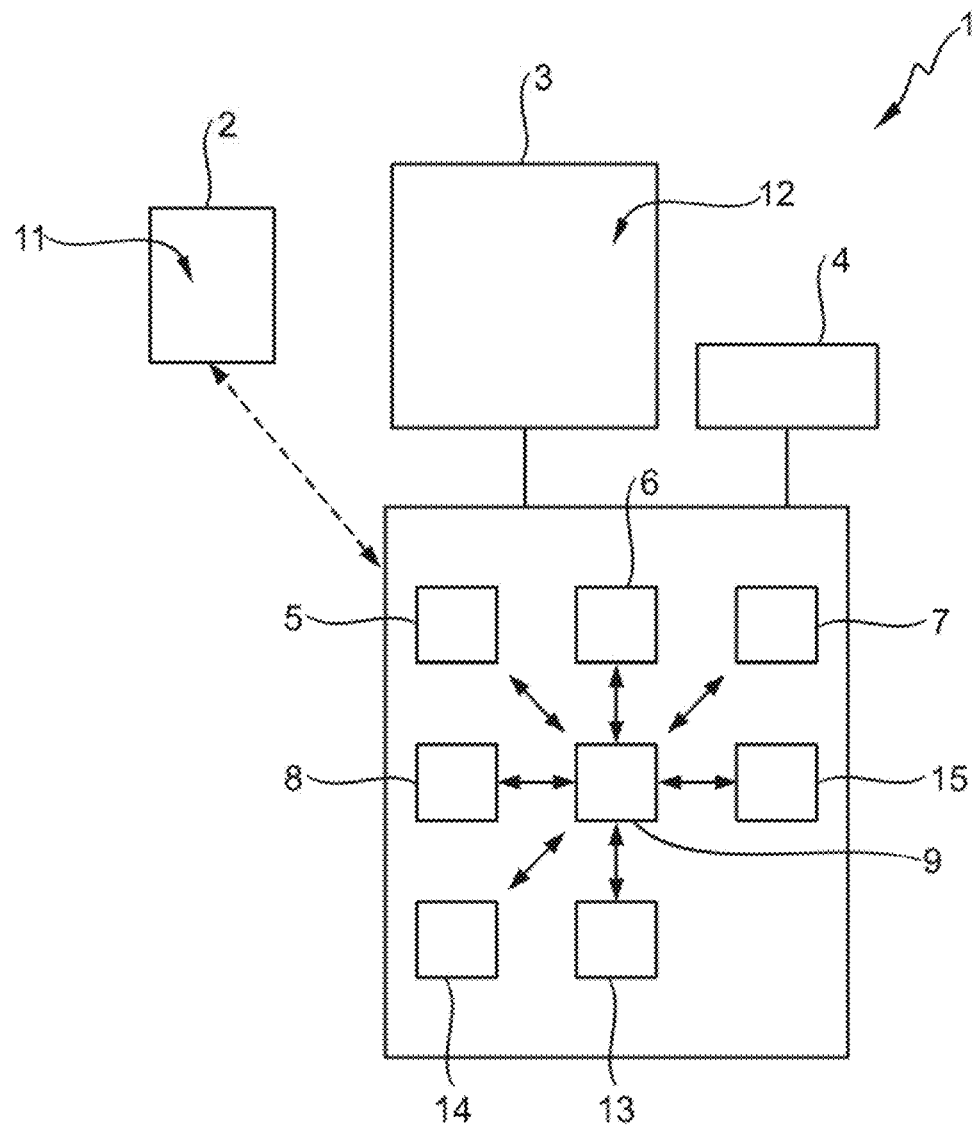
FIG. 1 shows schematically and exemplarily an embodiment of a displaying system for displaying DBT data.

A displaying system, a displaying method and a computer program which assist a radiologist in combining information from different DBT volume images of a woman's breast are provided.

In one example, a displaying system for displaying DBT data is presented, wherein the displaying system comprises:
an image providing unit for providing first and second DBT volume images of the left breast of a woman and first and second DBT volume images of the right breast of the woman, wherein the first DBT volume images correspond to at least one of a first image generation time and a first view and the second DBT volume images correspond to at least one of a second image generation time and a second view,
a navigation image providing unit for providing for each DBT volume image a respective two-dimensional navigation image,
a computer-aided detection (CAD) marker providing unit for providing for each DBT volume image a set of CAD markers, wherein each CAD marker is associated with a set of two-dimensional locations on the respective two-dimensional navigation image and a set of three-dimensional locations in the respective DBT volume image,
a correlation score providing unit for providing correlation scores being indicative of a likelihood that CAD markers of different DBT volume images of the same breast correspond to each other,
a display unit for displaying the navigation images and slices of the provided DBT volume images,
a user interface configured to allow a user to indicate a two-dimensional location on a navigation image, particularly displayed in a first display region which might be provided by the display unit, wherein this navigation image is regarded as being an activated navigation image and the DBT volume image, for which the activated navigation image has been provided, is regarded as being an activated DBT volume image of an activated breast,
a CAD marker determination unit for determining a CAD marker associated with the indicated two-dimensional location, wherein the determined CAD marker is regarded as being an activated CAD marker, and for determining another CAD marker of the other DBT volume image of the activated breast, which corresponds to the activated CAD marker, based on the provided correlation scores,
a slice determining unit for determining a first slice position defining a position of a slice of the activated DBT volume image, which includes a three-dimensional location of the activated CAD marker, and for determining a second slice position defining a position of a slice of the other DBT volume image, which includes a three-dimensional location of the other CAD marker,
a controller for controlling the display unit to display the slice of the activated DBT volume image at the determined first slice position and the slice of the activated DBT volume image at the determined second slice position, particularly in a second display region which might be provided by the display unit.

Thus, a user, for example, a radiologist can review the navigation images shown in the first display region and, if the user sees a suspicious region, the user can indicate the two-dimensional location of this suspicious region on the navigation image, whereupon automatically corresponding slices of the DBT volume images are shown on the display unit. This allows for a simpler and less time consuming combining of information from the different (separate and/or distinct) DBT volume images.

The display unit can be adapted to provide a first display region for displaying the navigation images and a second display region for displaying a slice of a provided DBT volume image, The image providing unit can be a storing unit in which the first and second DBT volume images are stored already and from which the first and second DBT volume images can be retrieved for providing the same. However, the image providing unit can also be a receiving unit for receiving the first and second DBT volume images from a DBT volume images acquisition device. The image providing unit can also be the DBT volume images acquisition device.

The first and second DBT volume images can correspond to different views, for instance, to a CC view and an MLO view. The DBT volume images can also refer to other views. Moreover, the first and second DBT volume images can refer to different image generation times. For instance, for each breast a current DBT volume image and an older DBT volume image can be provided. The image providing unit can provide two DBT volume images or more than two DBT volume images for each breast. It should be noted that the expressions "at least one of A and B" and "A and/or B" include a) A without B, b) B without A, and c) A and B.

In DBT imaging the respective breast is compressed just as in two-dimensional mammography, i.e. a DBT volume image is a three-dimensional image of a compressed breast. The view identification refers to the direction in which the breast is compressed, wherein the direction is the direction in which the breast would be compressed when a two-dimensional mammogram as indicated by the view would be generated. For instance, in CC views the beast is compressed with a horizontal compression paddle, while in MLO views the compression is done under an angle of, for instance, about 45 degrees.

Also the navigation image providing unit can be a storing unit, wherein in this case the navigation images are stored in the storing unit and the stored navigation images can be provided. The navigation image providing unit can also be adapted to generate the navigation images or to receive navigation images from another unit being adapted to generate the navigation images.

A navigation image is a two-dimensional image in which each two-dimensional location is assigned to at least one three-dimensional location in the corresponding DBT volume image, in order to allow navigating through the DBT volume image by indicating two-dimensional locations on the navigation image. The navigation image can be determined, for instance, by performing an artificial forward projection through the DBT volume image. In one example embodiment a mammogram can be rendered from an intersection of a surface fitted through locations within the respective DBT volume image, which are marked by CAD markers, and the respective DBT volume image, wherein the mammogram can be used as navigation image. One way of determining the navigation images is disclosed in the article "Generating Synthetic Mammograms From Reconstructed Tomosynthesis Volumes" by G. van Schie et al., IEEE Transactions on Medical Imaging, volume 32, pages 2322 to 2331 (2013), which is herewith incorporated by reference. The navigation image could also be regarded as being a synthetic image, i.e. a synthetic mammogram, which can also be named artificial mammogram.

Also the CAD marker providing unit can be a storing unit, wherein in this case CAD markers are stored in the storing unit and the stored CAD markers can be provided. However, the CAD marker providing unit can also be a receiving unit for receiving the CAD markers from another unit like a CAD marker generation unit and for providing the received CAD markers. The CAD marker providing unit can also be the CAD marker generation unit itself. In particular, the CAD marker providing unit can use known CAD algorithms for generating the CAD markers based on the provided DBT volume images.

Also the correlation score providing unit can be a storing unit, wherein in this case the correlation scores are stored in the storing unit and the stored correlation scores can be provided. The correlation score providing unit can also be a receiving unit for receiving correlation scores from a correlation score generation unit, or the correlation score providing unit can be the correlation score generation unit, wherein the generated correlation scores can be provided. The CAD marker providing unit and the correlation score providing unit can also be a same integrated unit, wherein this same integrated unit is adapted to provide the CAD markers and the correlation scores.

In one example embodiment the controller is further adapted to control the display unit to display a slice of the DBT volume image of the other breast, which corresponds to the at least one of the image generation time and view of the activated DBT volume image, at the determined first slice position and a slice of the DBT volume image of the other breast, which corresponds to the at least one of the image generation time and view of the other DBT volume image, at the determined second slice position. Moreover, the controller can be adapted to control the display unit to display a slice of the DBT volume image of the other breast, which corresponds to the at least one of the image generation time and view of the activated DBT volume image, at the determined first slice position, if the CAD marker determination unit has determined that no other CAD marker of the other DBT volume image of the activated breast corresponds to the activated CAD marker. Furthermore, also the slices of the DBT volume images, which correspond to the other of the at least one of the image generation time and view of the activated DBT volume image, at the determined first slice position can be determined and displayed. For instance, if the activated DBT volume image is a first DBT volume image, slices of the second DBT volume images can be shown at the first determined depth position. The advantage of this, compared to not performing any action, is to show at least a slice that will likely be close to the corresponding spatially correlated one. This fallback is based on the assumption that DBT volume images acquired in the same women are spatially correlated, especially the ones of the same breast. It is also possible to use other ways to do this fallback, for instance, using a spatial transformation given by a registration or mapping algorithm. If it has been determined that there is a corresponding CAD marker of the other DBT volume image of the activated breast, a corresponding slice of the other DBT volume image can be determined and shown.

In order to improve the spatial correlation between DBT volume images of a same breast, they can be spatially registered to each other by using known registration algorithms. Also for improving the spatial correlation between DBT volume images of the same view, but of different breasts, the DBT volume images can be registered to each other by using known registration algorithms.

The controller can be further adapted to control the display unit to show the activated marker on the activated navigation image. The CAD marker providing unit can be adapted to provide for each CAD marker a malignancy value being indicative of a probability of malignancy at the set of three-dimensional locations associated with the CAD marker within the respective DBT volume image, wherein the controller is adapted to control the display unit to show also an indication of malignancy on the activated navigation image based on the malignancy value provided for the activated CAD marker. The controller can also be adapted to control the display unit to show the other CAD marker on the navigation image of the other DBT volume image. Moreover, the controller can be adapted to control the display unit to show also an indication of malignancy on a navigation image, which corresponds to the other DBT volume image, based on the malignancy value provided for the other CAD marker. By also showing the CAD markers and indicating the probability of malignancy the assistance of the user in reviewing the DBT volume images can be further improved.

The display unit may comprise a stationary display and a non-stationary display, wherein a first display region is on the non-stationary display and a second display region is on the stationary display. The non-stationary display is typically a display of a tablet computer. The stationary display is typically a monitor of a workstation to be arranged, for instance, on a table. This allows for a provision of more space for displaying the DBT volume images, i.e. slices of the DBT volume images, on the stationary display, because the navigation images are not shown on the stationary display, but on the non-stationary display. Moreover, displaying the navigations images on the non-stationary display, particularly on a display of a tablet computer, can give a more natural feeling of interaction and can be more intuitive.

The controller can be further adapted to control the displaying system such that the user is allowed to subsequently indicate different two-dimensional locations on a navigation image, to check whether based on a previous indication of a two-dimensional location on a navigation image a CAD marker is shown, and to, if a CAD marker is shown, remove the CAD marker. This can ensure that the user is not distracted by already reviewed CAD markers, thereby further improving the assistance of the user in reviewing the DBT volume images.

Also the controller can be adapted to control the displaying system such that the user is allowed to subsequently indicate different two-dimensional locations on the navigation images, wherein the displaying system further comprises a CAD tracking unit for tracking CAD markers shown to the user, wherein the controller is further adapted to control the display unit to display all CAD markers, which have been provided by the CAD marker providing unit, for which a malignancy value has been provided being indicative of a probability of malignancy being larger than a predefined probability threshold and which have not been tracked by the CAD tracking unit, in the first display region, wherein these CAD markers are regarded as being unvisited CAD markers. Moreover, the controller can be adapted to control the display unit such that the unvisited CAD markers are displayed subsequently, wherein the respective unvisited CAD marker is shown on the respective navigation image at the respective two-dimensional location, wherein the slice determining unit is adapted to determine a slice position defining a position of a slice of the DBT volume image, which includes a three-dimensional location of the respective unvisited CAD marker, and the controller is adapted to control the display unit to display the slice of the DBT volume image at the determined slice position. In particular, the controller is adapted to control the display unit to display a next unvisited CAD marker, after the user has indicated via the user interface that the next unvisited CAD marker is to be displayed or after a current CAD marker has been displayed for a predefined time period. This can ensure that the user does not miss a possibly malignant region, which should be investigated, thereby further improving the assistance of the user in reviewing the DBT volume images. In a further aspect a displaying method for displaying DBT data is presented, wherein the displaying method comprises:

providing first and second DBT volume images of the left breast of a woman and first and second DBT volume images of the right breast of the woman by an image providing unit, wherein the first DBT volume images correspond to at least one of a first image generation time and a first view and the second DBT volume images correspond to at least one of a second image generation time and a second view, providing for each DBT volume image a respective two-dimensional navigation image by a navigation image providing unit, providing for each DBT volume image a set of CAD markers by a CAD marker providing unit, wherein each CAD marker is associated with a set of two-dimensional locations on the respective two-dimensional navigation image and a set of three-dimensional locations in the respective DBT volume image, providing correlation scores being indicative of a likelihood that CAD markers of different DBT volume images of the same breast correspond to each other by a correlation score providing unit, facilitating a user indicating a two-dimensional location on a navigation image displayed on a display unit by a user interface, wherein this navigation image is regarded as being an activated navigation image and the DBT volume image, for which the activated navigation image has been provided, is regarded as being an activated DBT volume image of an activated breast, determining a CAD marker associated with the indicated two-dimensional location by a CAD marker determination unit, wherein the determined CAD marker is regarded as being an activated CAD marker, and determining another CAD marker of the other DBT volume image of the activated breast, which corresponds to the activated CAD marker, based on the provided correlation scores, determining a first slice position defining a position of a slice of the activated DBT volume image, which includes a three-dimensional location of the activated CAD marker, and determining a second slice position defining a position of a slice of the other DBT volume image, which includes a three-dimensional location of the other CAD marker, by a slice determining unit, controlling the display unit to display the slice of the activated DBT volume image at the determined first slice position and the slice of the other DBT volume image at the determined second slice position in a second display region of the display unit by a controller.

In another aspect a computer readable storage medium storing a computer program for displaying DBT data is provided, wherein the computer program comprises program code means or instructions or logic for causing a displaying system, for example as defined in claim 1, to carry out the steps of the displaying method, for example as defined in claim 13, when the computer program is run on a computer controlling the displaying system.

It shall be understood that the displaying system, the displaying method, and the computer readable storage medium, may have similar and/or identical embodiments.

It shall be understood that example embodiments can also be any combination of the subject matter described herein.

These and other aspects will be apparent from and elucidated with reference to the example embodiments described hereinafter.

FIG. 1 shows schematically and exemplarily an embodiment of a displaying system for displaying DBT data. The displaying system 1 comprises an image providing unit 5 for providing a CC DBT volume image and an MLO DBT volume image of a women's left breast and a CC DBT volume image and an MLO DBT volume image of a women's right breast. The displaying system 1 further comprises a navigation image providing unit 6 for providing for each DBT volume image a respective two-dimensional navigation image and a CAD marker providing unit 7 for providing for each DBT volume image a set of CAD markers, wherein each CAD marker is associated with a set of two-dimensional locations on the respective two-dimensional navigation image and a set of three-dimensional locations in the respective DBT volume image. The CAD markers mark CAD regions, wherein the CAD regions cover the respective set of two-dimensional locations on the respective two-dimensional navigation image and the respective set of three-dimensional locations in the respective DBT volume image. For instance, for each DBT volume image 5 to 10 CAD markers may be provided.

The image providing unit 5 can be adapted to provide the DBT volume images such that they are spatially correlated. The DBT volume images are each formed of slices arranged at different depth positions. The DBT volume images are provided such that slices of different DBT volume images of the same breast show at least partly the same part of the same breast. Moreover, the DBT volume images are provided such that slices of DBT volume images of the same view, but of different breasts, at the same depth position show at least partly corresponding parts in the left breast and the right breast.

Moreover, the displaying system 1 comprises a correlation score providing unit 8 for providing correlation scores being indicative of a likelihood that CAD markers of different DBT volume images of the same breast correspond to each other. For providing the navigation images, the CAD markers and the correlation scores known algorithms can be used like the algorithms disclosed in the articles "Mass detection in reconstructed digital breast tomosynthesis volumes with a computer-aided detection system trained on 2D mammograms" by G. van Schie et al., Medical Physics, volume 40 (2013) and "Generating Synthetic Mammograms From Reconstructed Tomosynthesis Volumes" by G. van Schie et al., IEEE Transactions on Medical Imaging, volume 32, pages 2322 to 2331 (2013), which are herewith incorporated by reference.

The displaying system 1 further comprises a display unit with a stationary display 3, which in this example embodiment may be regarded as being a main display, and a non-stationary display 2 which in this example embodiment is a tablet display device. The stationary display 3 is typically a monitor of a workstation. The displaying system 1 also comprises an input unit 4 like a keyboard, a computer mouse, etcetera, which is adapted to allow a user like a radiologist to provide inputs into the displaying system 1.

The non-stationary display 2 comprises a first display region 11 and the stationary display 3 comprises a second display region 12. The first display region 11 is touch sensitive, in order to allow a user like a radiologist to indicate a two-dimensional location on a navigation image displayed in the first display region by touching the location. In another example embodiment for indicating a two-dimensional location on a navigation image also other means can be used like a mouse pointer. The touch sensitive first display region 11 forms a user interface 2 via which the two-dimensional location on the navigation image can be indicated by the user.

Figure 2:
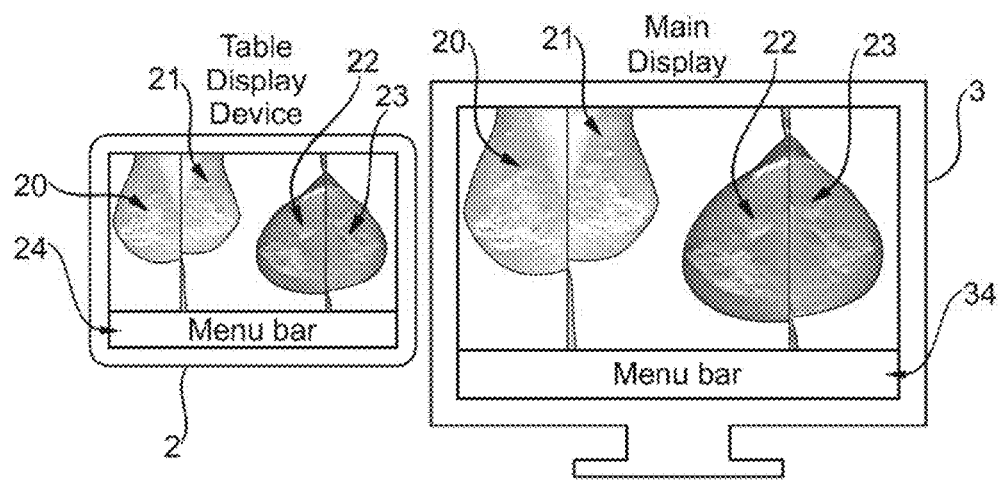
FIG. 2 illustrates schematically and exemplarily a stationary display and a non-stationary display showing navigation images.

FIG. 2 shows schematically and exemplarily the non-stationary display 2 with four navigation images 20 ... 23 and the stationary display 3 also showing the navigation images 20 ... 23. Moreover, optionally menu bars 24, 34 can be shown on the displays 2, 3. The menu bars 24, 34 can provide tools for modifying the navigation images 20 ... 23.

Figure 3:
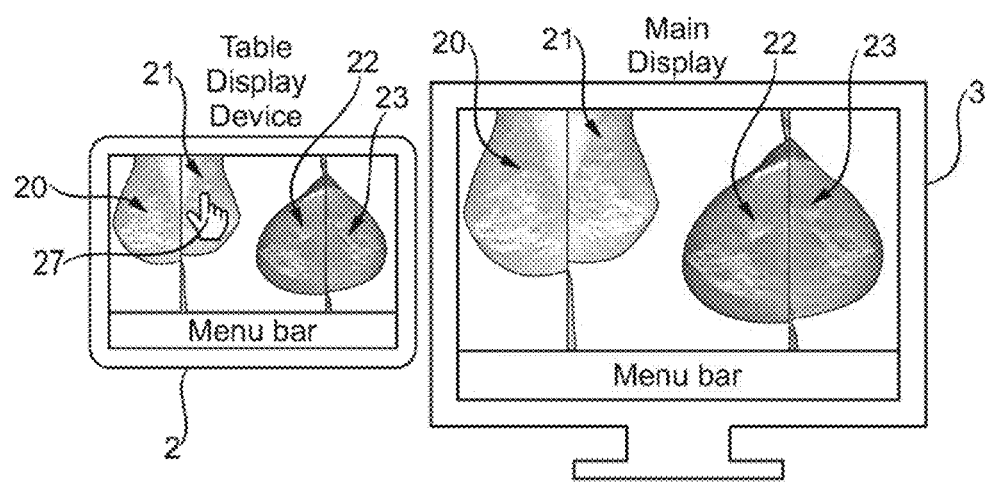
FIG. 3 illustrates schematically and exemplarily an indication of a two-dimensional location in a navigation image shown on the non-stationary display.

FIG. 3 is similar to FIG. 2, but in addition it illustrates that a user indicates a two-dimensional location on the navigation image 21 shown on the non-stationary display 2. This indication of the two-dimensional location on the navigation image 21 is illustrated by the hand 27. Hence, the user can search for abnormalities in the navigation images 20 ... 23 shown by the non-stationary display 2 and the stationary display 3 and, if an abnormality is seen, the user, who can also be regarded as being a reader, can click on a two-dimensional location on a navigation image like the navigation image 21 shown on the non-stationary display 2. The navigation image 21, on which the two-dimensional location has been indicated, is regarded as being an activated navigation image. The activated navigation image 21 is associated with a CC DBT volume image or an MLO DBT volume image and a breast i.e. the right breast or the left breast of the woman. The associated DBT volume image is regarded as being an activated DBT volume image and the breast is regarded as being an activated breast.

The displaying system 1 further comprises a CAD marker determination unit 14 for determining a CAD marker 30 associated with the indicated two-dimensional location, wherein the determined CAD marker is regarded as being an activated CAD marker. Moreover, the CAD marker determination unit 14 is adapted to determine another CAD marker 31 of another DBT volume image of the activated breast, which corresponds to the activated CAD marker 30, based on the provided correlation scores. In particular, the CAD marker determination unit 14 is adapted to determine another CAD marker, for which the highest correlation score has been provided for a correlation with the activated CAD marker, wherein, in order to ensure that the two CAD markers really correspond to each other, the correlation score should also be larger than a predefined correlation score threshold. Thus, the CAD marker determination unit 14 can be adapted to determine which other CAD markers have a correlation score for a combination with the activated CAD marker being larger than the correlation score threshold, wherein among the resulting other CAD markers having correlation scores being larger than the correlation score threshold the CAD marker can be selected having the largest correlation score. It can also be the other way around, i.e. firstly determining the other CAD marker having the largest correlation score with the activated CAD marker and then determining whether this correlation score is larger than the predefined correlation score threshold.

The displaying system 1 further comprises a slice determining unit 15 for determining a first slice position z defining a position of a slice 41 of the activated DBT volume image, which includes a three-dimensional location of the activated CAD marker 30, and for determining a second slice position $z_c$ defining a position of a slice 43 of the other DBT volume image which includes a three-dimensional location of the other CAD marker 30.

Figure 4:
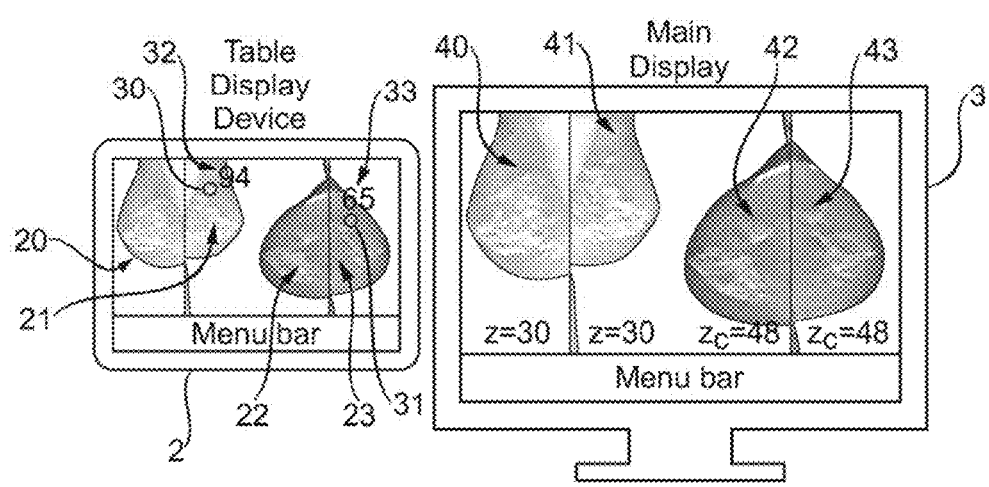
FIG. 4 illustrates schematically and exemplarily CAD markers on navigation images shown on the non-stationary display and corresponding slices of DBT volume images shown on the stationary display.

Moreover, the displaying system 1 comprises a controller 9 for controlling the displaying system, in particular the different components of the displaying system. For instance, the controller 9 is adapted to control the non-stationary display 2 and the stationary display 3 such that the slice 41 of the activated DBT volume image at the determined first slice position z and the slice 43 of the other DBT volume image at the determined second slice position $z_c$ are shown in the second display region 12. This is schematically and exemplarily illustrated in FIG. 4.

The controller 9 is further adapted to control the non-stationary display 2 to show the activated marker 30 on the activated navigation image 21 and the other CAD marker 31 on the corresponding navigation image 23 of the other DBT volume image in the first display region 11. The controller 9 is also adapted to control the non-stationary display 2 to show an indication 32 of malignancy on the activated navigation image 21 based on a malignancy value provided for the activated CAD marker 30 and to show an indication 33 of malignancy on a navigation image 23, which corresponds to the other DBT volume image, based on a malignancy value provided for the other CAD marker 31 in the first display region 11 on the non-stationary display 2. The malignancy values are indicative of a probability of malignancy at the set of three-dimensional locations associated with the respective CAD marker. The malignancy values are also provided by the CAD marker providing unit 7. The controller 9 can be further adapted to control the stationary display 3 to display a slice of the other DBT volume image at the determined first slice position z and a slice of the activated DBT volume image at the determined second slice position $z_c$ in the second display region 12.

The controller 9 can further be adapted to control the displays 2, 3 such that, if the CAD marker determination unit 14 has determined that no other CAD marker of the other DBT volume image of the activated breast corresponds to the activated CAD marker 30, a slice of the other DBT volume image at the determined first slice position z is displayed in the second display region 12.

Thus, a slice of the activated DBT volume image at the first slice position z can be shown in a corresponding viewer, wherein the first slice position z is set to, for instance, the depth location within the activated DBT volume image where the activated CAD marker was detected in the activated DBT volume image. If a corresponding CAD region, i.e. a region marked by another CAD marker, is found in another DBT volume image of another view being different to the view of the activated DBT volume image of the same activated breast at a second slice position $z_c$, also the slice at the first depth position z of the other DBT volume image of the same breast can be shown on the main display. Moreover, slices at the second position $z_c$ of DBT volume images of both breasts in the DBT volume images of the other view can be shown on the main display 3. If a corresponding CAD region, i.e. a corresponding CAD marker covering a corresponding CAD region, is not found, slices at the first positions z of all DBT volume images can be shown.

The controller 9 is further adapted to control the decision support system 1 such that the user is allowed to subsequently indicate different two-dimensional locations on the navigation images 20 . . . 23, to check whether based on a previous indication of a two-dimensional location on one of the navigation images 20 . . . 23 a CAD marker is shown in the first display region 11 and to, if a CAD marker is shown in the first display region 11, remove the CAD marker in the first display region 11. Thus, before reviewing a next CAD marker, previous CAD markers are removed. When reviewing a CAD marker, the user can add comments to the CAD marker into the displaying system 1 via the input unit 4. These comments can later be provided as a report about the reviewing of the DBT volume images, in particular of the CAD markers.

The displaying system 1 further comprises a CAD tracking unit 13 for tracking CAD markers shown to the users, wherein the controller 9 is further adapted to control the display unit to display all CAD markers, which have been provided by the CAD marker providing unit 7, for which a malignancy value has been provided being indicative of a probability of malignancy being larger than a predefined probability threshold and which have not been tracked by the CAD tracking unit 13, in the first display region 11, wherein these CAD markers are regarded as being unvisited CAD markers. In particular, the controller 9 is adapted to control the display unit such that the unvisited CAD markers are displayed subsequently, wherein the respective unvisited CAD marker is shown on the respective navigation image in the first display region 11 at the respective two-dimensional location. The slice determining unit 15 is adapted to determine a slice position defining a position of a slice of the DBT volume image, which includes a three-dimensional location of the respective unvisited CAD marker, and the controller 9 is adapted to control the display unit to display the slice of the DBT volume image at the determined slice position in the second display region 12. As explained above with respect to the activated CAD marker, also regarding the respective unvisited CAD marker the above described techniques for selecting certain slices of the DBT volume images, in particular by using a corresponding CAD marker, can be applied. Thus, the displaying system 1 keeps track of all visited CAD markers, wherein, when the user, i.e. a reader, is finished with reading, the displaying system 1 can collect all unvisited CAD markers with malignancy scores being larger than a given threshold. Unvisited CAD markers can be systematically displayed on the non-stationary display 2 followed by the synchronized display of informative slices of the DBT volume images on the stationary display 3 as described above. This displaying can be performed via a "next button" mode, a "cine mode", or another mode. Thus, for instance, the controller 9 can be adapted to control the non-stationary display 2 to display a next unvisited CAD marker, after the user has indicated, for example, via the touch sensitive surface of the non-stationary display 2 or the input unit 4 that the next unvisited CAD marker is to be displayed or after a current CAD marker has been displayed for a predefined time period.

Figure 5:
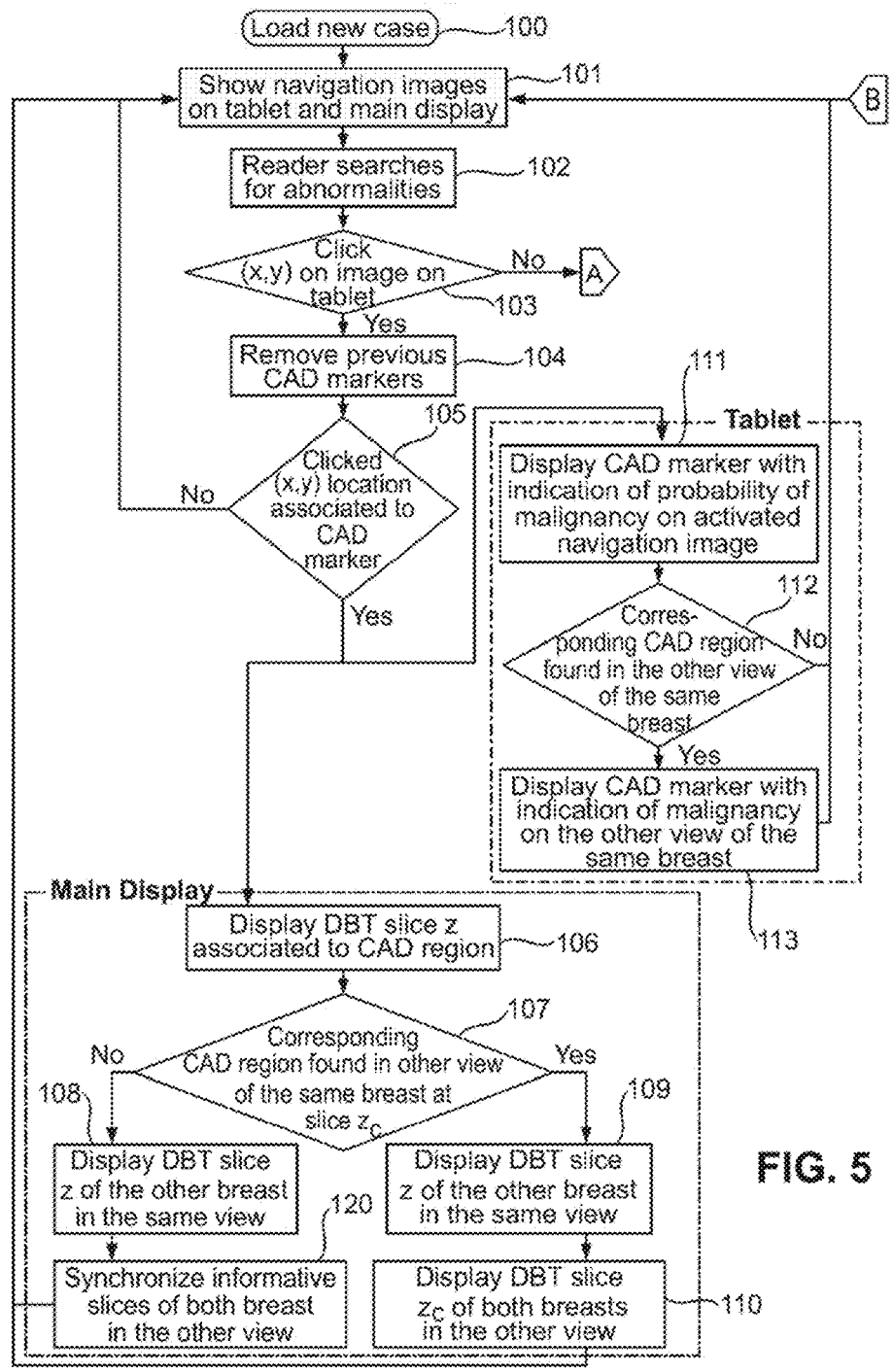
FIGS. 5 and 6 show a flowchart exemplarily illustrating an embodiment of a displaying method for displaying DBT data.
Figure 6:
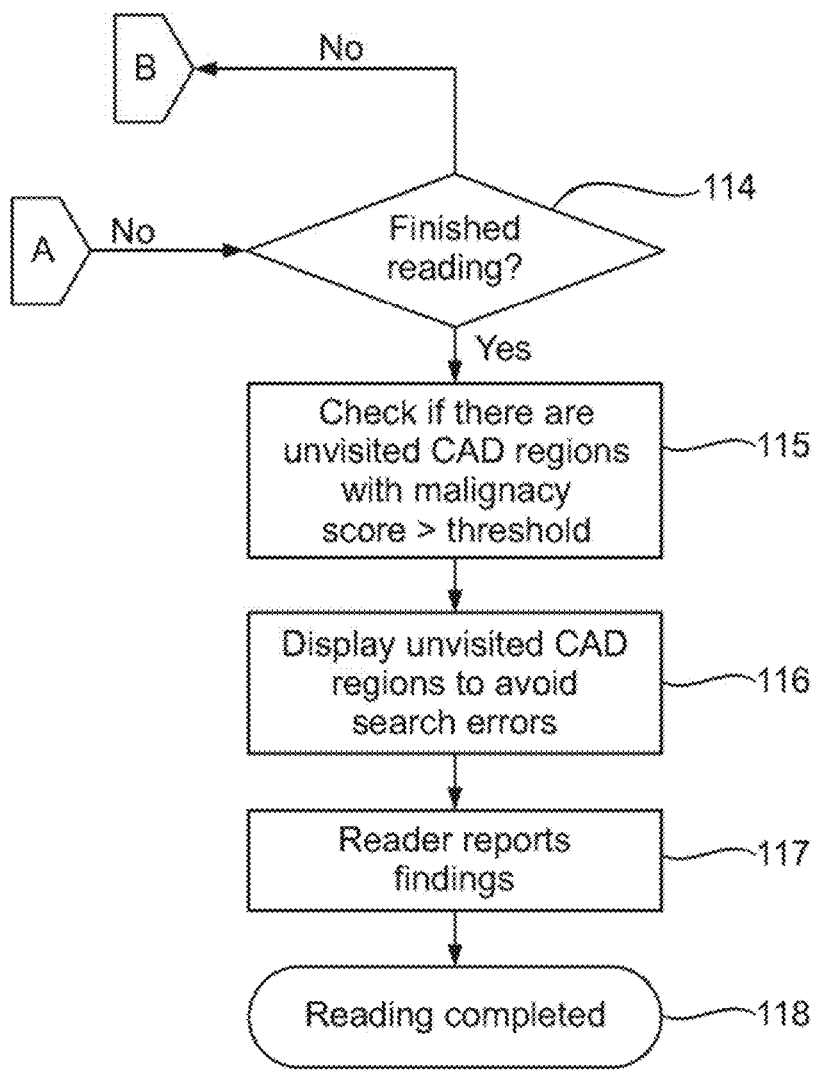

In the following an example embodiment of a displaying method for displaying DBT data will exemplarily be described with reference to a flowchart shown in FIGS. 5 and 6.

In step (e.g., block) 100 a new case is loaded. The loaded case includes different DBT volume images corresponding to different views of the left and right breasts of a woman, respective two-dimensional navigation images, CAD markers associated with a set of two-dimensional locations on a respective two-dimensional navigation image and a set of three-dimensional locations in a respective DBT volume image, and correlation scores being indicative of a likelihood that CAD markers of different DBT volume images of a same breast correspond to each other.

In step 101 the navigation images are shown on the non-stationary display and the stationary display, whereafter in step 102 a reader can search for abnormalities and in step 103 it is determined whether the reader has indicated a two-dimensional location on a navigation image on the non-stationary display 2. If this is not the case, it is determined whether the reading has been finished in step 114 and wherein, if the reading has not been finished, the method continues with step 101. Thus, steps 101, 102, 103 and 114 are carried out in a loop, if the reader does not indicate a two-dimensional location on a navigation image and the reading has not been finished. The displaying system can allow the reader to indicate via, for instance, a button in the menu bar 24 whether the reading is finished, wherein this input may be used in step 114.

If in step 103 a two-dimensional location has been indicated on a navigation image on the non-stationary display 2, in step 104 previous CAD markers, if present, are removed and in step 105 it is determined whether the indicated location is associated with a CAD marker. If this is not the case, the method continues with step 101. Otherwise, the method proceeds with steps 106 and 111.

The associated CAD marker is regarded as being an activated CAD marker, the DBT volume image comprising the activated CAD marker is regarded as being an activated DBT volume image and the navigation image, on which the two-dimensional location has been indicated, is regarded as being an activated navigation image. In step 106 a first slice position z defining a position of a slice of the activated DBT volume image, which includes a three-dimensional location of the activated CAD marker, is determined and shown on the stationary display 3. Thus, a DBT slice at the first slice position z, which is associated with the CAD region marked by the active CAD marker, is displayed. In step 107 it is determined whether a corresponding CAD marker can be found in the other DBT volume image of the same breast, wherein, if this is the case, a second slice position $z_c$ defining a position of a slice of the other DBT volume image, which includes a three-dimensional location of the other CAD marker, is determined. Moreover, if a corresponding CAD marker has been found, in step 109 the DBT slice z of the other breast in the same view is displayed, i.e. in the view which corresponds to the view of the activated DBT volume image, and in step 110 DBT slices $z_c$ of both breasts are shown in the other view, i.e. the view not being the view of the activated DBT volume image. Thus, if a CAD marker is present at a certain slice position within a DBT volume image of a certain view and of a certain breast, this certain slice and in addition a slice at the certain slice position of the other DBT volume image of the certain view and of the other breast can be displayed. So, if a CAD marker is found in a breast and the correspond informative slice is displayed, the displaying system can immediately display a corresponding slice or a slice which is very close to the corresponding slice of the contralateral breast, in order to allow a radiologist to compare both breasts for finding asymmetries that might point to suspicious regions, without requiring the radiologist to, for instance, search for the slices in the large DBT volume images.

If in step 107 a corresponding CAD marker has not been found, in step 108 the DBT slice z of the other breast in the same view is displayed, i.e. in the view which corresponds to the view of the activated DBT volume image, and in step 120 informative slices of both breasts in the other view are synchronized. This means, for instance, the slices at the first slice position z of the DBT volume images of the other view are displayed, in order to show the slices at the first slice position z of all DBT volume images of both breasts. Alternatively, if the DBT volume images of different views are not spatially correlated, the slice determination unit can be adapted to determine spatially correlated slices in the DBT volume images of the other view by using a known registration algorithm, wherein these determined slices might be shown in step 120. In a further example embodiment in step 120 the navigation images of the DBT volume images of the other view are still displayed or arbitrary slices of the DBT volume images of the other view are shown.

In step 111 on the non-stationary display the activated CAD marker is shown together with an indication of the probability of malignancy on the activated navigation image. In step 112 it is determined whether a corresponding CAD region has been found in the other DBT volume image of the same breast, wherein, if this is the case, in step 113 the corresponding CAD marker is shown on the non-stationary display 2 together with an indication of malignancy on a navigation image of the other view of the same breast. If a corresponding CAD region could not be found, step 101 follows step 112.

If the reader has indicated that he wants to finish the reading, in step 115 it is checked if there are unvisited CAD regions, i.e. unvisited CAD markers, with a malignancy score, i.e. with a malignancy value provided by the CAD marker providing unit 7, being larger than a predefined threshold. If this is the case, these unvisited CAD regions are shown to the reader in step 116, whereafter the display system 1 allows the reader to report findings in step 117. Steps 116 and 117 can be carried out in a loop, wherein, each time the steps of the loop are performed, in step 116 a visualization in accordance with above steps 106 to 113 can be provided for the respective unvisited CAD marker and in step 117 reports can be added by the user for the respective unvisited CAD marker. The method ends in step 118.

The display system can be adapted to allow the user, i.e. the reader, to have a look at the slices by, for instance, scrolling through the slices, of one or several of the DBT volume images, before going to step 101. This may lead to an improved lesion assessment.

Since the displaying system and method described above with reference to FIGS. 1 to 6 does not only allow the reader to review the DBT volume images, but to also provide comments to suspicious regions marked by CAD markers such that the reader can interactively review the DBT volume images and generate a report which might include decisions regarding, for instance, cancer, the displaying system and method can also be regarded as being a decision support system and method, respectively. The displaying system and method are adapted to aid a radiologist in reading and interpreting findings in DBT volume images. The displaying system and method use CAD region or CAD marker correlations between DBT volume images of different views of the same breast, in order to navigate to informative slices of especially all DBT volume images displayed on the stationary display which can be regarded as being a main display. For displaying the navigation images, which can also be regarded as being CAD navigation images, the non-stationary display is used, which can be a tablet display device.

Although in above described example embodiments the display unit comprises a tablet display device and a main display, i.e. a monitor of a workstation, in another example embodiment the display unit may only comprise the main display such that the navigation images and the DBT volume images are both shown on the main display. The main display may comprise a respective viewer for each provided DBT volume image, i.e., for instance, four viewers for showing CC and MLO DBT volume images of the left and right breast. For navigation purposes in each viewer a corresponding navigation image may be shown as a transparent, color-coded overlay on a respective slice of a respective DBT volume image. It is also possible that in each viewer only the respective navigation image is shown without an underlying slice of the respective DBT volume image. The user can indicate a two-dimensional location on a shown navigation image, whereafter one or several CAD markers and slice positions can be determined and the slices of the DBT volumes images at the determined slice positions can be displayed in the viewers as described above, for instance, with respect to steps 106 to 110 and 120. The input unit can be adapted to allow the user to indicate, if he/she wants to see again the navigation images in the viewers, in order to allow him/her to indicate another two-dimensional location in a navigation image. For example, a button, a mouse gesture, a key combination can be input into the system, in order to indicate that the navigation images should be shown again. This input could also be regarded as being a shortcut back to the navigation images. It is also possible that, after the user has indicated a two-dimensional location on a shown navigation image, firstly it is determined whether an associated CAD marker is present, especially as described above with reference to step 105, wherein, if this is the case, this CAD marker is shown optionally together with an indication of malignancy on the navigation image. If a corresponding CAD marker can be determined, especially as described above with reference to step 107, also this corresponding CAD marker can be shown on the corresponding navigation image optionally together with an indication of malignancy. In this example slices of DBT volume images at corresponding slice positions are only displayed, especially in accordance with above steps 106 to 110 and 120, after the user has indicated that he/she wants to see the slices by providing a corresponding input like a single our double left mouse button click, a right mouse button click, et cetera. Also a shortcut to the navigation images can be provided via a further input.

In another example embodiment the tablet display device can be replaced by additional views on the main display device, i.e. views being in addition to views showing the DBT volume images or by a separate screen. Moreover, the interaction with the tablet display device or its possible replacement can be performed using a touch pad device or another additional device like a keyboard or a computer mouse. The CAD regions, i.e. the CAD markers, displayed on the non-stationary display can point to soft tissue like masses, architectural distortions, asymmetries, et cetera and/or to microcalcification lesions. Moreover, one or several CAD regions or CAD markers can also be displayed on the stationary display, i.e. on the slices of the DBT volume images.

The displaying system can be adapted to allow the user to modify the thickness of the slices of the DBT volume images, in order to reduce the total number of slices. This can lead to a further reduced reading time of the user. For instance, on the main display a graphical user interface can be provided allowing or facilitating the user to modify the slice thickness. The images providing unit 5 might be adapted to modify the DBT volume images accordingly For instance, a mean intensity projection can be applied for every "X" slices, in order to increase the thickness of the slices, wherein the parameter "X" might be input by the user.

Although in above described embodiments the DBT volume images correspond to CC and MLO views, in other example embodiments also other views can be used like mediolateral (ML) views. Moreover, although in above described embodiments for each breast only two DBT volume images corresponding to two different views are provided, in other example embodiments more than two DBT volume images for more than two views can be provided for each breast. Correspondingly, the visualization on the displays 2, 3 is not limited to four images per display.

Although in above described embodiments the different DBT volume images of a same breast correspond to different views, in other example embodiments the different DBT volume images of a same breast can be different with respect to another parameter like the time. In particular, the different DBT volume images of a same breast can relate to a same view but to different acquisition times.

Other variations to the described example embodiments are contemplated.

In the claims, the word "comprising" does not exclude other elements or steps, and the indefinite article "a" or "an" does not exclude a plurality.

One or more general purpose virtual or physical computing systems suitably instructed or a special purpose computing system may be used to implement the displaying system. Further, the displaying system may be implemented in software, hardware, firmware, or in some combination to achieve the capabilities described herein. Note that one or more general purpose or special purpose computing systems/devices may be used to implement the described techniques. However, just because it is possible to implement the displaying system on a general purpose computing system does not mean that the techniques themselves or the operations required to implement the techniques are conventional or well known.

Also, the embodiments described above may also use well-known or proprietary, synchronous or asynchronous client-server computing techniques. Also, the various components may be implemented using more monolithic programming techniques, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously and communicate using message passing techniques. Equivalent synchronous embodiments are also supported Also the example embodiments may be implemented in a distributed environment comprising multiple, even heterogeneous, computer systems and networks. Different configurations and locations of programs and data are contemplated for use with techniques of described herein. In addition, the components may be physical or virtual computing systems and may reside on the same physical system. Also, one or more of the modules may themselves be distributed, pooled or otherwise grouped, such as for load balancing, reliability or security reasons.

A single unit or device may fulfill the functions of several items recited in the claims. The mere fact that certain measures are recited in mutually different dependent claims does not indicate that a combination of these measures cannot be used.

Operations like the provision of a CAD marker, the provision of a correlation score, the provision of a navigation image, the determination of a CAD marker, the determination of a slice, et cetera performed by one or several units or devices can also be performed by any other number of units or devices. These operations and/or the control of the displaying system in accordance with the displaying method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Some or all of the components of the displaying system may be implemented or provided in other manners, such as at least partially in firmware and/or hardware, including, but not limited to one or more application-specific integrated circuits (ASICs), standard integrated circuits, controllers executing appropriate instructions, and including microcontrollers and/or embedded controllers, field-programmable gate arrays (FPGAs), complex programmable logic devices (CPLDs), and the like. Some or all of the system components and/or data structures may also be stored as contents (e.g., as executable or other machine-readable software instructions or structured data) on a computer-readable medium (e.g., a hard disk; memory; network; other computer-readable medium; or other portable media article to be read by an appropriate drive or via an appropriate connection, such as a DVD or flash memory device) to enable the computer-readable medium to execute or otherwise use or provide the contents to perform at least some of the described techniques. Some or all of the components and/or data structures may be stored on tangible, non-transitory storage mediums.

Any reference signs in the claims should not be construed as limiting the scope.

The embodiments described relate to a displaying system for displaying DBT data. First and second DBT volume images of the left breast of a woman and first and second DBT volume images of the right breast of the woman are provided by an image providing unit. Moreover, for each DBT volume image a two-dimensional navigation image is provided by a navigation image providing unit, wherein a user is allowed to indicate a location in the navigation image by using a user interface, whereafter a CAD marker associated with the location is determined in a DBT volume image of a breast and a corresponding CAD marker, if present, is determined in another DBT volume image of the breast. Slices of these DBT volume images, which are associated with the CAD markers, are presented on a display.

All of the above U.S. patents, U.S. patent application publications, U.S. patent applications, foreign patents, foreign patent applications and non-patent publications referred to in this specification and/or listed in the Application Data Sheet are incorporated herein by reference, in their entireties.

From the foregoing it will be appreciated that, although specific embodiments have been described herein for purposes of illustration, various modifications may be made without deviating from the spirit and scope of the invention. For example, the methods, techniques, and systems for displaying digital breast tomosynthesis (DBT) data discussed herein are applicable to multiple computer system and machine architectures. Also, the methods and systems discussed herein are applicable to differing protocols, communication media (optical, wireless, cable, etc.) and devices (such as wireless handsets, electronic organizers, personal digital assistants, portable email machines, game machines, pagers, navigation devices such as GPS receivers, etc.).

The invention claimed is:

1. A displaying system for displaying digital breast tomosynthesis (DBT) data, the displaying system comprising:
   an image providing unit configured to provide first and second DBT volume images of the left breast of a woman and first and second DBT volume images of the right breast of the woman, wherein the first DBT volume images correspond to at least one of a first image generation time and a first view and the second DBT volume images correspond to at least one of a second image generation time and a second view;
   a navigation image providing unit configured to provide for each DBT volume image a respective two-dimensional navigation image;
   a computer-aided detection (CAD) marker providing unit configured to provide for each DBT volume image a set of CAD markers, wherein each CAD marker is associated with a set of two-dimensional locations on the respective two-dimensional navigation image and a set of three-dimensional locations in the respective DBT volume image;
   a correlation score providing unit configured to provide correlation scores being indicative of a likelihood that CAD markers of different DBT volume images of the same breast correspond to each other;
   a display unit configured to display the navigation images and slices of the provided DBT volume images;
   a user interface configured to allow a user to indicate a two-dimensional location on a navigation image displayed, wherein this navigation image is regarded as being an activated navigation image and the DBT volume image, for which the activated navigation image has been provided, is regarded as being an activated DBT volume image of an activated breast;
   a CAD marker determination unit configured to determine a CAD marker associated with the indicated two-dimensional location, wherein the determined CAD marker is regarded as being an activated CAD marker, and for determining another CAD marker of the other DBT volume image of the activated breast, which corresponds to the activated CAD marker, based on the provided correlation scores;
   a slice determining unit configured to determine a first slice position (z) defining a position of a slice of the activated DBT volume image, which includes a three-dimensional location of the activated CAD marker, and configured to determine a second slice position ($z_c$) defining a position of a slice of the other DBT volume image, which includes a three-dimensional location of the other CAD marker; and
   a controller configured to control the display unit to display the slice of the activated DBT volume image at the determined first slice position (z) and the slice of the other DBT volume image at the determined second slice position ($z_c$).

2. The system of claim 1, wherein the controller is further adapted to control the display unit to display a slice of the DBT volume image of the other breast, which corresponds to the at least one of the image generation time and view of the activated DBT volume image, at the determined first slice position (z) and a slice of the DBT volume image of the other breast, which corresponds to the at least one of the image generation time and view of the other DBT volume image, at the determined second slice position ($z_c$).

3. The system of claim 1, wherein the controller is further adapted to control the display unit to display a slice of the DBT volume image of the other breast, which corresponds to the at least one of the image generation time and view of the activated DBT volume image, at the determined first slice position (z), if the CAD marker determination unit has determined that no other CAD marker of the other DBT volume image of the activated breast corresponds to the activated CAD marker.

4. The system of claim 1 wherein the controller is further adapted to control the display unit to show the activated marker on the activated navigation image.

5. The system of claim 1 wherein the CAD marker providing unit is adapted to provide for each CAD marker a malignancy value being indicative of a probability of malignancy at the set of three-dimensional locations associated with the CAD marker within the respective DBT volume image, wherein the controller is adapted to control the display unit to show also an indication of malignancy on the activated navigation image based on the malignancy value provided for the activated CAD marker.

6. The system of claim 1 wherein the controller is further adapted to control the display unit to show the other CAD marker on the navigation image of the other DBT volume image.

7. The system of claim 1 wherein the CAD marker providing unit is adapted to provide for each CAD marker a malignancy value being indicative of a probability of malignancy at the set of three-dimensional locations associated with the CAD marker within the respective DBT volume image, wherein the controller is adapted to control the display unit to show also an indication of malignancy on a navigation image, which corresponds to the other DBT volume image, based on the malignancy value provided for the other CAD marker.

8. The system of claim 1 wherein the display unit is adapted to provide a first display region for displaying the navigation images and a second display region for displaying a slice of a provided DBT volume image and comprises a stationary display and a non-stationary display, wherein the first display region is on the non-stationary display and the second display region is on the stationary display.

9. The system of claim 1 wherein the controller is further adapted to control the displaying system such that the user is allowed to subsequently indicate different two-dimensional locations on a navigation image, to check whether based on a previous indication of a two-dimensional location on a navigation image a CAD marker is shown, and to, if a CAD marker is shown in the first display region, remove the CAD marker.

10. The system of claim 1 wherein the CAD marker providing unit is adapted to provide for each CAD marker a malignancy value being indicative of a probability of malignancy at the location of the respective CAD marker within the respective DBT volume image, wherein the controller is adapted to control the displaying system such that the user is allowed to subsequently indicate different two-dimensional locations on the navigation images, wherein the displaying system further comprises a CAD tracking unit configured to track CAD markers shown to the user, wherein the controller is further adapted to control the display unit to display all CAD markers, which have been provided by the CAD marker providing unit, for which a malignancy value has been provided being indicative of a probability of malignancy being larger than a predefined probability threshold and which have not been tracked by the CAD tracking unit, wherein these CAD markers are regarded as being unvisited CAD markers.

11. The system of claim 10, wherein the controller is adapted to control the display unit such that the unvisited CAD markers are displayed subsequently, wherein the respective unvisited CAD marker is shown on the respective navigation image at the respective two-dimensional location, wherein the slice determining unit is adapted to determine a slice position defining a position of a slice of the DBT volume image, which includes a three-dimensional location of the respective unvisited CAD marker, and the controller is adapted to control the display unit to display the slice of the DBT volume image at the determined slice position.

12. The system of claim 10 wherein the controller is adapted to control the display unit to display a next unvisited CAD marker, after the user has indicated via the user interface that the next unvisited CAD marker is to be displayed or after a current CAD marker has been displayed for a predefined time period.

13. A displaying method for displaying DBT data, the displaying method comprising:
providing first and second DBT volume images of the left breast of a woman and first and second DBT volume images of the right breast of the woman by an image providing unit, wherein the first DBT volume images correspond to at least one of a first image generation time and a first view and the second DBT volume images correspond to at least one of a second image generation time and a second view;
providing for each DBT volume image a respective two-dimensional navigation image by a navigation image providing unit;
providing for each DBT volume image a set of CAD markers by a CAD marker providing unit, wherein each CAD marker is associated with a set of two-dimensional locations on the respective two-dimensional navigation image and a set of three-dimensional locations in the respective DBT volume image;
providing correlation scores being indicative of a likelihood that CAD markers of different DBT volume images of the same breast correspond to each other by a correlation score providing unit;
facilitating a user indicating a two-dimensional location on a navigation image displayed on a display unit by a user interface, wherein this navigation image is regarded as being an activated navigation image and the DBT volume image, for which the activated navigation image has been provided, is regarded as being an activated DBT volume image of an activated breast;
determining a CAD marker associated with the indicated two-dimensional location by a CAD marker determination unit, wherein the determined CAD marker is regarded as being an activated CAD marker, and determining another CAD marker of the other DBT volume image of the activated breast, which corresponds to the activated CAD marker, based on the provided correlation scores;
determining a first slice position (z) defining a position of a slice of the activated DBT volume image, which includes a three-dimensional location of the activated CAD marker, and determining a second slice position ($z_c$) defining a position of a slice of the other DBT volume image, which includes a three-dimensional location of the other CAD marker, by a slice determining unit; and controlling the display unit to display the slice of the activated DBT volume image at the determined first slice position (z) and the slice of the other DBT volume image at the determined second slice position ($z_c$).

14. A computer-readable storage medium containing instructions for controlling a computer processor to display DBT data, the instructions comprising program code logic for performing a method comprising:

providing first and second DBT volume images of the left breast of a woman and first and second DBT volume images of the right breast of the woman by an image providing unit, wherein the first DBT volume images correspond to at least one of a first image generation time and a first view and the second DBT volume images correspond to at least one of a second image generation time and a second view;

providing for each DBT volume image a respective two-dimensional navigation image by a navigation image providing unit;

providing for each DBT volume image a set of CAD markers by a CAD marker providing unit, wherein each CAD marker is associated with a set of two-dimensional locations on the respective two-dimensional navigation image and a set of three-dimensional locations in the respective DBT volume image;

providing correlation scores being indicative of a likelihood that CAD markers of different DBT volume images of the same breast correspond to each other by a correlation score providing unit;

facilitating a user indicating a two-dimensional location on a navigation image displayed on a display unit by a user interface, wherein this navigation image is regarded as being an activated navigation image and the DBT volume image, for which the activated navigation image has been provided, is regarded as being an activated DBT volume image of an activated breast;

determining a CAD marker associated with the indicated two-dimensional location by a CAD marker determination unit, wherein the determined CAD marker is regarded as being an activated CAD marker, and determining another CAD marker of the other DBT volume image of the activated breast, which corresponds to the activated CAD marker, based on the provided correlation scores;

determining a first slice position (z) defining a position of a slice of the activated DBT volume image, which includes a three-dimensional location of the activated CAD marker, and determining a second slice position ($z_c$) defining a position of a slice of the other DBT volume image, which includes a three-dimensional location of the other CAD marker, by a slice determining unit; and controlling the display unit to display the slice of the activated DBT volume image at the determined first slice position (z) and the slice of the other DBT volume image at the determined second slice position ($z_c$).

15. The computer-readable storage medium of claim 14 provided as part of a computing system.

16. The computer-readable storage medium of claim 14, the method further comprising controlling the display unit to display a slice of the DBT volume image of the other breast, which corresponds to the at least one of the image generation time and view of the activated DBT volume image, at the determined first slice position (z) and a slice of the DBT volume image of the other breast, which corresponds to the at least one of the image generation time and view of the other DBT volume image, at the determined second slice position ($z_c$).

17. The computer-readable storage medium of claim 14, the method further comprising controlling the display unit to display a slice of the DBT volume image of the other breast, which corresponds to the at least one of the image generation time and view of the activated DBT volume image, at the determined first slice position (z), if the CAD marker determination unit has determined that no other CAD marker of the other DBT volume image of the activated breast corresponds to the activated CAD marker.

18. The computer-readable storage medium of claim 14, the method further comprising controlling the display unit to show the activated marker on the activated navigation image.

19. The computer-readable storage medium of claim 14, the method further comprising:

providing for each CAD marker a malignancy value being indicative of a probability of malignancy at the set of three-dimensional locations associated with the CAD marker within the respective DBT volume image; and controlling the display unit to show also an indication of malignancy on the activated navigation image based on the malignancy value provided for the activated CAD marker.

20. The computer-readable storage medium of claim 14, the method further comprising controlling the display unit to show the other CAD marker on the navigation image of the other DBT volume image.

* * * * *